US007927878B2

(12) United States Patent
Kremer et al.

(10) Patent No.: US 7,927,878 B2
(45) Date of Patent: Apr. 19, 2011

(54) PROCESS FOR THE DETERMINATION OF LIPOPROTEINS IN BODY FLUIDS

(75) Inventors: Werner Kremer, Pentling (DE); Hans Robert Kalbitzer, Regensburg (DE); Fritz Huber, Regensburg (DE)

(73) Assignee: LipoFIT Analytic GmbH, Regensburg (DE)

( * ) Notice: Subject to any disclaimer, the term of this patent is extended or adjusted under 35 U.S.C. 154(b) by 1146 days.

(21) Appl. No.: 11/628,168

(22) PCT Filed: Jun. 1, 2005

(86) PCT No.: PCT/EP2005/005886
§ 371 (c)(1),
(2), (4) Date: Nov. 30, 2006

(87) PCT Pub. No.: WO2005/119285
PCT Pub. Date: Dec. 15, 2005

(65) Prior Publication Data
US 2008/0038829 A1     Feb. 14, 2008

Related U.S. Application Data

(60) Provisional application No. 60/576,173, filed on Jun. 1, 2004.

(30) Foreign Application Priority Data

Jun. 1, 2004     (DE) .......................... 10 2004 026 903

(51) Int. Cl.
*G01N 33/92* (2006.01)
*G01N 24/08* (2006.01)
(52) U.S. Cl. ........... 436/71; 436/63; 436/173; 422/68.1; 702/19; 702/22; 702/23; 702/32; 324/307; 324/308; 324/312
(58) Field of Classification Search ............ 436/63, 436/71, 173; 702/19, 22, 23, 32; 324/307, 324/308, 312; 422/68.1, 82.05
See application file for complete search history.

(56) References Cited

U.S. PATENT DOCUMENTS

| | | | |
|---|---|---|---|
| 4,933,844 A | 6/1990 | Otvos | |
| 5,343,389 A | 8/1994 | Otvos | |
| 6,576,471 B2 | 6/2003 | Otvos | |
| 6,617,167 B2 | 9/2003 | Otvos et al. | |
| 6,653,140 B2 | 11/2003 | Otvos | |
| 2003/0054559 A1 | 3/2003 | Otvos et al. | |
| 2004/0142496 A1* | 7/2004 | Nicholson et al. | ............ 436/536 |
| 2006/0183234 A1* | 8/2006 | Otvos | .............. 436/71 |

FOREIGN PATENT DOCUMENTS

| EP | 0 361 214 B1 | 7/1994 |
|---|---|---|
| WO | WO 93/03450 | 2/1993 |
| WO | WO 03/012416 A1 | 2/2003 |

OTHER PUBLICATIONS

Analytica, Munchen 11.-14.05 2004, Halle A 5, Stand A5.251-A5. 350 bzw.A5.261-A5.360, *Beteiligunng der Bayerischen Universitäten an der Analytica 2004*, Exponate der Analytica 2002 pp. 1-5; Bayern Innovativ-Analytica 2004 pp. 1-3.
Kapital 3, Kernresonanz-Spektren, Hesse M. et al, vol. 4, p. 132.
Clin. Chem. 37/3, 377-386 (1991), *Quantification of Plasma Lipoproteins by Proton Nuclear Magnetic Resonance Spectroscopy*, J.D. Otvos, E.J. Jeyarajah and D.W. Bennett.
*Low-Density Lipoprotein Particle Concentration and Size as Determined by Nuclear Magnetic Resonance Spectroscopy as Predictors of Cardiovascular Disease in Women*, Gavin J. Blake, MB, MSc, MRCPI; James D. Otvos, PhD; Nader Rifai, PhD; Paul M. Ridker, MD, MPH, pp. 14:11 Nov. 29, 2006, pp. 2-9, 2002.
*Nuclear Magnetic resonance chromatography: applications of pulse field gradient diffusion NMR to mixture analysis and ligand-receptor interactions*, John S. Gounarides, Aidi Chen, Michael J. Shapiro, Journal of Chromatography B. 725 (1999) 79-90.
*Nuclear Magnetic Resonance Spectroscopy of Lipoproteins and Risk of Coronary Heart Disease in the Cardiovascular Health Study*, Lewis Kuller, Alice Arnold, Russell Tracy, James Otvos, Greg Burke, Bruce Psaty, David Siscovick, David S. Freedman, Richard Kronmal, Arterioscler Thromb Vasc Biol., pp. 1175-1180, Jul. 2002.
*Effects of pravastatin treatment on lipoprotein subclass profiles and particle size in the PLAC-I trial*, James D. Otvos$^{a,b}$, Irina Shalaurova$^{a,b}$, David S. Freedman$^{c}$, Robert S. Rosensond$^{d,*}$, Atherosclerosis 160 (2002) 41, 48, Department of Biochemistry, North Carolina State University, Raleigh, NC, Jul. 14, 2000; revised form Apr. 6, 2001; accepted Apr. 30, 2001.
*Relations of Lipoprotein Subclass Levels and Low-Density Lipoprotein Size to Progression of Coronary Artery Disease in the Pravastatin Limitation of Atherosclerosis in the Coronary Arteries (PLAC-1) Trial*, Robert S. Rosenson, MD, James D. Otvos, PhD, and David S. Freedman, PhD., 2002 by Excerpta Medico, Inc., The American Journal of Cardiology vol. 90 Jul. 15, 2002, pp. 89-94.
*Analysis of Biofluids and Chemical Mixtures in Non-deuterated Solvents with $^{1}$H Diffusion-Weighted PFG Phase-Sensitive Double-Quantum NMR Spectroscopy*, Claudio Daivit and Jean Marc Böhlen, NMR in Biomedicine, vol. 10, 285-291 (1997), XP009052972.
*Proton magnetic resonance spectroscopy of fractionated plasma lipoproteins and reconstituted plasma from healthy subjects and patients with cancer*, T. Emngan, K.S. Bjerve, A.L. H0E & J. Krane, Departments of Oncology and Radiotherapy and Clinical Chemistry, University Hospital of Trondheim, and The Center for Nuclear Magnetic Resonance, SINTEF, UNIMED, Trondheim, Norway, pp. 393-408, XP009052938, 1992.

(Continued)

*Primary Examiner* — Maureen M Wallenhorst
(74) *Attorney, Agent, or Firm* — Cohen Pontani Lieberman & Pavane LLP

(57) ABSTRACT

The invention describes a process for the determination of the concentration distribution and size distribution of lipoprotein classes in body fluids, e.g. blood. For this purpose, NMR spectra of a sample to be analysed are measured by magnetic field gradient intensities and temperatures under different diffusion-weighted measuring conditions selected according to different pulse programs (e.g. PFG-STE, PFG-LED etc) and consequently in a differentiated manner according to the relaxation times. The different effects of these measuring conditions on the intensity/line form of the NMR signals of the individual lipoprotein classes are determined and permit the determination of a concentration distribution/size distribution of the individual lipoprotein classes.

22 Claims, 7 Drawing Sheets

OTHER PUBLICATIONS

*750 MHz $^1$H-NMR spectroscopy of human blood plasma*, P.J.D. Foxall, M. Spraul, R.D. Farrant, L.C. Lindon, G.H. Neild and J.K. Nicholson, Journal of Pharmaceutical & Biomedical Analysis, vol. 11, No. 4/5, pp. 267-276, 1993, XP-002342275.

*750 MHz $^1$H and $^1$H-$^{13}$C NMR Spectroscopy of Human Blood Plasma*, Jeremy K. Nicholson and Peta J.D. Foxall, Departmetn of Chemistry, Birkbeck College, University of London, Gordon House, 29 Gordon Square, London WC1H OPP, U.K., Analytical Chemistry, vol. 67, No. 5, Mar. 1, 1995, pp. 793-811.

*Biomolecular NMR Spectroscopy, 2—Methods for spectral assignment—multidimensional NMR*, Jeremy N.S. Evans 1995, Oxford University Press, New York, pp. 55-98.

*Fourier Transform Pulsed-Gradient Spin-Echo Studies of Molecular Diffusion*, Peter Stilbs, Institute of Physical Chemistry, Uppaala University, Swedon, Progress in NMR Spectroscopy, vol. 19, pp. 1-45, 1987.

\* cited by examiner

|  | LDL [A] | |
|---|---|---|
|  | Methyl | Methylene |
| Standard without gradient | 1,000 | 1,150 |
| Standard gradient [A] | 0,200 | 0,230 |
| Standard gradient [B] | 0,120 | 0,138 |
| Standard gradient [C] | 0,030 | 0,035 |
| Line width | 0,017 | 0,017 |
| Shift [ppm] | 0,885 | 1,285 |
| Line proportion Lorentz | 100% | 100% |
| Line proportion Gauss | 0% | 0% |

FIG 10

| Lipoprotein classes and subclasses | Relative conzentration | Shift Methyl | Shift Methylen | Size [nm] | | Density [g/ml] | |
|---|---|---|---|---|---|---|---|
| | | | | min. | max. | max. | min. |
| Chylomicron [C] | 1,93 | 0,930 | 1,350 | 1000 | 10000 | 0,930 | 0,900 |
| Chylomicron [B] | 40,80 | 0,920 | 1,340 | 500 | 1000 | 0,940 | 0,930 |
| Chylomicron [A] | 37,34 | 0,910 | 1,320 | 100 | 500 | 0,960 | 0,940 |
| Chylo remnants | 2,07 | 0,900 | 1,310 | 70 | 100 | 1,010 | 1,000 |
| VLDL [C] | 38,93 | 0,920 | 1,320 | 80 | 90 | 0,970 | 0,960 |
| VLDL [B] | 41,17 | 0,910 | 1,310 | 70 | 80 | 0,985 | 0,970 |
| VLDL [A] | 23,70 | 0,900 | 1,300 | 60 | 70 | 1,000 | 0,985 |
| IDL | 8,72 | 0,897 | 1,297 | 40 | 60 | 1,010 | 1,000 |
| LDL [C] | 26,34 | 0,895 | 1,295 | 32 | 40 | 1,020 | 1,010 |
| LDL [B] | 20,05 | 0,890 | 1,290 | 24 | 32 | 1,040 | 1,020 |
| LDL [A] | 18,96 | 0,885 | 1,285 | 16 | 24 | 1,060 | 1,040 |
| LDL (small Dense) | 5,77 | 0,885 | 1,270 | 16 | 24 | 1,040 | 1,020 |
| Lp(a) | 4,53 | 0,880 | 1,265 | 16 | 30 | 1,100 | 1,050 |
| HDL2 | 98,16 | 0,880 | 1,265 | 7 | 16 | 1,180 | 1,060 |
| HDL3 | 153,59 | 0,870 | 1,260 | 4 | 7 | 1,240 | 1,180 |

| Other components | Relative concentration | Shift [A] | Shift [B] | Size [nm] | | Density [g/ml] | |
|---|---|---|---|---|---|---|---|
| | | | | min. | max. | max. | min. |
| LPDS 1 | 10194,54 | 1,380 | - | 0,1 | 4 | 0,95 | 1,1 |
| LPDS 2 | 510,01 | 0,960 | - | 0,1 | 4 | 0,95 | 1,1 |
| LPDS 3 | 0,00 | 0,000 | - | 0,1 | 4 | 0,95 | 1,1 |
| Lactate | 38,38 | 1,365 | 1,350 | 0,1 | 0,1 | 1 | 1 |
| Unsaturated FS[A] | 56,234 | 1,620 | - | - | - | - | - |
| Unsaturated FS[B] | 35,278 | 2,050 | - | - | - | - | - |

PROCESS FOR THE DETERMINATION OF LIPOPROTEINS IN BODY FLUIDS

PRIORITY CLAIM

This is a U.S. national stage of application No. PCT/EP2005/005886, filed on Jun. 1, 2005. Priority is claimed on the following application(s): Country: U.S. Application No. 60/576,173, Filed: Jun. 1, 2004; Country: Germany, Application No.: 10 2004 026 903.3, Filed: Jun. 1, 2004; the contents of which are incorporated here by reference.

FIELD OF INVENTION

The present invention relates to a process for the determination of the density and size distribution of lipoproteins in body fluids and to an apparatus for carrying out this process.

BACKGROUND OF THE INVENTION

Arteriosclerosis which, inter alia, is attributable to cholesterol deposits in the arterial vascular walls is one of the most frequent causes of death in the industrialised nations of the West. Depending on where the deposits occur, impairment of blood circulation in the brain (stroke), impairment of blood circulation in the heart (coronary heart disease, myocardial infarction) and arterial occlusive diseases in the peripheral arteries may occur. Investigations have shown that the risk of suffering from arteriosclerosis corresponds to the proportion of cholesterol present in the blood. This cholesterol is present in the form of lipoprotein particles which contain cholesterol, for example, together with proteins. These lipoproteins effect the transport of the water-insoluble lipids in the blood. Lipoproteins can be subdivided into different lipoprotein classes, inter alia, on the basis of their density, lipid components and apolipoproteins. The risk of suffering from arteriosclerosis appears to correlate to a high level of LDL (low density lipoprotein) cholesterol. In contrast, cholesterol in HDL particles (high density lipoprotein) seems to contribute to the removal of arteriosclerotic plaques in arterial vascular walls. Further investigations indicate that certain size and density distributions within lipoprotein classes are a good indicator for the early recognition of cardiovascular diseases and the risk of suffering of arteriosclerosis (Kuller et al., (2002), Nuclear Magnetic Resonance spectroscopy of lipoproteins and risk of coronary heart disease in the cardiovascular health study, Aterioscler. Thromb. Vasc. Biol. 22, 1175-1180; Blake et al., (2002), Low-density lipoprotein particle concentration and size as determined by nuclear magnetic resonance spectroscopy as predictors of cardiovascular disease in women, Circulation 106, 1930-1937; Rosenson et al., (2002), Relations of lipoprotein subclass levels and low-density lipoprotein size to progression of coronary artery disease in the pravastatin limitation of arteriosclerosis in the coronary arteries (PLAC-I Trial), Am. J. Cardiol. 90, 89-94; Rosenson et al., (2002), Effects of pravastatin treatment on lipoprotein subclass profiles and particle size in the PLAC-I trial, arteriosclerosis 160, 41-48). For this reason, numerous lipoprotein determinations in the blood are carried out for the early recognition of cardiovascular diseases. It is assumed that the object of up to 60-80% of the diagnostic blood tests in the laboratory is, at least partially, the determination of lipoprotein.

From EP 0 361 214 B1, a process for the determination of the concentration of four lipoproteins in a blood plasma sample by NMR measurements is known. In this process, the line contour of an NMR spectrum of a plasma sample to be analysed is fitted by a weighted linear combination of the four lipoprotein reference spectra. By refining the weighting coefficients of the individual reference spectra, the concentrations of the four lipoprotein components can be calculated. In the case of this process, however, no size distributions and density distributions can be determined within one lipoprotein class.

In the review article "Nuclear magnetic resonance chromatography: applications of pulse field gradient diffusion NMR to mixture analysis and ligand-receptor interaction", Journal of chromatography B; 725 (1999), pages 79-90, a complicated process for investigating protein-ligand interactions is disclosed in the case of which proteins specifically $^{13}C/^{15}N$-labelled for NMR spectroscopy are used, apart from pulse field gradient NMR.

SUMMARY OF THE INVENTION

It is one object of the present invention to provide a process for the determination, in particular classification and quantification, of lipoproteins in body fluids and an apparatus for carrying out this process which are improved with respect to the above-mentioned disadvantages.

This object is achieved according to the invention by a process according to claim 1. Advantageous aspects of the process and an apparatus for carrying out the process are the subject matter of further claims.

One embodiment of the invention describes a process for the determination, in particular the classification and quantification, of lipoproteins in body fluids. For this purpose, NMR spectra of a sample of the body fluid to be analysed are measured under different measuring conditions. The different measuring conditions are selected in such a way that they permit the separation of superimposing inhomogeneous NMR resonance lines of different lipoprotein classes. By varying the measuring conditions, a diffusion-weighted one-dimensional and multidimensional magnetic nuclear resonance spectroscopy (NMR) with pulsed magnetic field gradients is implemented. These different measuring conditions are selected from different magnetic field gradients and varying temperatures. For this purpose, several NMR spectra are recorded e.g. for one plasma or serum sample at different magnetic field gradients and/or different temperatures in each case. The varying effects of the different magnetic field gradients and different temperatures on the form of the signal, e.g. the intensity and/or line width of the NMR signals of the individual lipoprotein classes are subsequently determined and a certain density distribution and size distribution is assigned to the individual lipoprotein classes on the basis of the different effects.

In one embodiment a process according to the invention can be improved by varying other parameters such as the composition of the sample (solvent, chemical modifications). For this purpose, several NMR spectra are, as a rule, recorded and analysed jointly under different conditions.

The process can be used to analyse a wide variety of different specimens from body fluids, e.g. blood plasma and blood serum samples of any desired origin. Suitable body fluids in this respect are all lipoprotein-containing body fluids of different origins, e.g. blood, lymph or spinal cord fluid. The process allows the analysis of NMR signals of inhomogeneous composition in NMR spectra attributable to the varying inhomogeneous distribution within lipoprotein classes. Thus, the proportions of cholesterol, the density distribution and size distribution of the particles within a lipoprotein class can vary e.g. depending on the constitution of a patient.

The size distribution of lipoprotein particles within a lipoprotein class, e.g. HDL or LDL particles, can be determined according to one aspect of the invention by applying different magnetic field gradients, additionally to the high frequency pulses, to produce diffusion-weighted NMR spectra of the sample to be analysed, e.g. a blood sample. This can be done by producing an additional locally varying magnetic field in the sample e.g. by using gradient coils in addition to the magnetic field already present in the NMR spectrometer.

A spin echo experiment, wherein a magnetic field gradient is additionally produced is shown schematically in FIG. 2 as merely one possible example of diffusion-weighted NMR spectroscopy. During this spin echo experiment, the magnetisation caused by spins of the hydrogen atoms is first rotated into the detection plane by a so-called 90° pulse ($\pi/2$) and detected. In this detection plane, the magnetisation of individual spin packages is subsequently dephasing. Lipoprotein particles, for example, diffuse to a different extent due to their different sizes. If, during this period, a so-called magnetic field gradient is applied along the z-field of the sample, in addition to the existing magnetic field, the different lipoprotein particles are subject to the influence of different magnetic field strengths as a result of their different size and consequently their different diffusion behaviour. If a 180° pulse, a $\pi$ pulse is applied, the magnetisation of the spins of those lipoproteins (the larger lipoprotein particles, e.g. VLDL particles=very low density lipoproteins) is refocused which did not diffuse too far during the dephasing of the spins. Smaller lipoprotein particles, HDL particles for example, have already diffused further during this period and are subject to the influence of another z-field strength such that their magnetisation by the 180° pulse can be refocused only insufficiently or, depending on the strength of the magnetic field gradient, not at all. This has the consequence that, as a function of the magnetic field gradient applied, NMR signals of smaller lipoprotein particles can be selectively suppressed and/or the intensity of these signals reduced in a defined manner (see for example also FIGS. 3 and 6). Apart from this spin echo experiment, a large number of other pulse sequences are possible in the case of variants of processes according to the invention.

From FIG. 10, it can be learned that, within a lipoprotein class, the size of the lipoprotein particles varies (e.g. in the case of the sub-class division of LDL [A] to LDL [C] chosen by the inventors). The above-mentioned diffusion-weighted magnetic field gradient measuring method thus also offers a possibility for determining the size distribution within lipoprotein classes and/or lipoprotein sub-classes. This size distribution can also be an indicator of the personal risk of cardiovascular disease (Kuller et al., (2002), Nuclear Magnetic Resonance spectroscopy of lipoproteins and risk of coronary heart disease in the cardiovascular health study, Aterioscler. Thromb. Vasc. Biol. 22, 1175-1180; Blake et al., (2002), Low-density lipoprotein particle concentration and size as determined by nuclear magnetic resonance spectroscopy as predictors of cardiovascular disease in women, Circulation 106, 1930-1937; Rosenson et al., (2002), Relations of lipoprotein subclass levels and low-density lipoprotein size to progression of coronary artery disease in the pravastatin limitation of arteriosclerosis in the coronary arteries (PLAC-I Trial), Am. J. Cardiol. 90, 89-94; Rosenson et al., (2002), Effects of pravastatin treatment on lipoprotein subclass profiles and particle size in the PLAC-I trial, arteriosclerosis 160, 41-48).

By means of one embodiment of a process according to the invention, during which different magnetic field gradients are applied to the sample to be analysed, it is, for example, also possible to detect lipoprotein classes which had previously been difficult to detect, e.g. Lp(a) and small dense LDL which are classified as being highly dangerous with respect to the risk of cardiovascular disease (compare also FIG. 1).

Moreover, in one embodiment of a process according to the invention, it is possible to vary the measuring temperatures as further measuring conditions. Variations in the measuring temperatures exert, above all, an influence on the line width of the NMR signals of the lipoprotein particles and their components. At a rising temperature, the line width of the NMR signals can become narrower (change in the transverse relaxation time T2) since the lipoprotein particles become more mobile at rising temperature, the longitudinal relaxation time T1 and the transverse relaxation time T2 normally becoming greater. Depending on the gradient pulse sequence selected, a T1 and T2 weighting can be introduced in a defined manner in addition to the diffusion weighting. In the case of particularly densely packed particles, e.g. HDL particles, a temperature increase generally does not exert as strong an influence as in the case of less densely packed particles, e.g. LDL or VLDL particles. This has the consequence that, in the case of differently densely packed lipoprotein particles, a change in temperature has a different effect on the change on the line widths of the NMR signals of the lipoprotein particles concerned. Thus, it is possible by means of one embodiment according to the invention to determine a density distribution within the lipoprotein classes. Typical measuring temperatures would in this case be temperatures of approximately 278 K, 298 K, 308 K and 318 K.

In one embodiment of a process according to the invention it is possible to simultaneously vary the magnetic field gradient and the measuring temperature. However, it is also possible to change only the magnetic field gradient at a constant temperature or vice versa to change only the measuring temperature with a constant magnetic field. Apart from the simple spin echo method described above, all the methods described in the literature such as PFG-STE, PFG-LED etc. can be used for diffusion weighting.

In one advantageous embodiment of the process according to the invention, a multidimensional set of characteristic reference parameters of an NMR spectrum is determined for each lipoprotein class (see for example FIG. 9). This multidimensional set can be determined e.g. from a series of suitable recorded NMR spectra—one spectrum being recorded for each lipoprotein class in a borderline case. The characteristic reference parameters are selected from the distributions of the chemical shifts, the distributions of the NMR signal intensities, the distributions of the NMR signal widths and the line forms as a function of magnetic field gradients and other external parameters possible such as the temperature. By means of these characteristic reference parameters, it is possible to calculate NMR spectra and to fit them to the experimental spectra by means of multidimensional optimisation processes known in the literature.

Since the reference parameters are known or have been determined, it is possible, primarily, to determine from them the concentration of the lipoprotein particles of the different classes. Secondarily, it is possible to determine further physical and chemical properties within a class such as the lipid composition and the exact size of the lipoprotein particles.

In this embodiment of the process according to the invention, a so-called class function $f_i(G, \delta, p_1, \ldots, p_N)$, which is dependent on the gradient strength G, the chemical shift $\delta$ and other experimental parameters $p_j$ such as the temperature T, the pulse sequence used and the strength of the external magnetic field is obtained for each lipoprotein class i. The class function $f_i$ is then built up from the M base function $g_k$ as $$f_i = \sum_k^M g_k$$

$$= \sum_k^M a_k(G, \delta_k, p_1, \ldots, p_n, T_1^k(p_1, \ldots, p_n), T_2^k(p_1, \ldots, p_n)) \otimes$$

$$L(\delta, \Delta\delta_{1/2}^k)$$

(1)

with $a_k$ being a complex-valent function which describes the interaction between the amplitude and phase of parameters and $L(\delta)$ a line form function centred around $\delta=0$ (e.g. a Gauβ or Lorentz function with the width $\Delta\delta_{1/2}^k$). The entire experimental spectrum S can then be described for N classes with a concentration $c_i$ by $$S = \sum_i^N c_i f_i \quad (2)$$

For particles and free individual molecules of (approximately) equal size, the effect of the gradient intensity G in the class functions can be separated by $$f_i = \tilde{f}_i \cdot h_i(G) \quad (3)$$

In a simplification normally applicable, the effect dependent upon the particle size (more accurately upon the corresponding diffusion constant $D_i$) of the gradient intensity G is approximated by $$h_i = e^{-AD_i G^2} \quad (4)$$

The advantage of this embodiment of the process according to the invention consists in that the characteristic reference parameters characterise in each case the pure lipoprotein class and/or subclass and, can be adapted directly to the parameters of the NMR spectrometer used to record the NMR spectra such as the measuring frequency and magnetic field strength on the basis of basic physical considerations. In contrast, in the case of the above-mentioned measuring process described in the document EP 0 361 214 B1, the spectra of pure lipoprotein components measured on a specific NMR spectrometer are subjected to a summation using simple mathematical methods and varied in order to reconstruct in this way the experimentally measured spectrum of the blood sample to be analysed. Consequently, this process is much more strongly dependent on the specific measuring conditions, in particular the parameters, of the NMR spectrometer used. The present process according to the invention, on the other hand, can be carried out without problems on different NMR spectrometers with different frequencies due to the parametrisation using the characteristic reference parameters. The characteristic reference parameters are independent from the parameters of the apparatus used to record the spectra, e.g. the NMR spectrometer.

This variant of the process according to the invention is based on the consideration that particles of a given lipoprotein class are built up from different chemical components with different patterns of chemical shifts and relaxation times and are consequently characterised by inhomogeneous resonance lines but that particles of the same size provide the same response to the variation of the magnetic field gradients. This is exploited particularly well by the above process in order to separate lipoprotein classes spectroscopically and to describe them mathematically by the process described above. Under given experimental conditions, only the particle concentrations $c_i$ (see equation 2) need then be adjusted. This can be done reliably by almost any desired optimisation process.

Advantageously, a process according to one embodiment of the invention comprises the following process steps:

A) determining a parametrised NMR reference model for each lipoprotein class to be analysed, containing the characteristic reference parameters of the lipoprotein class and its behaviour under the various measuring conditions in each case.

Thereby, the effects of the different measuring conditions on the signal intensity and/or line width of each lipoprotein class are also calculated (see e.g. the effects of the magnetic field gradients on the signal intensity in the data set of FIG. 9).

Subsequently, NMR spectra of a plasma or serum sample to be analysed are recorded in a process step B) under the different measuring conditions used in A). In a process step C), the density distribution and/or size distribution are subsequently determined for each lipoprotein class on the basis of a weighting of the reference parameters.

An NMR reference data set determined in process step A) is shown in FIG. 9 for the lipoprotein subclass LDL [A] so named by the inventors. Such an NMR reference data set can be obtained, for example, by recording, NMR reference spectra for each lipoprotein class to be analysed under the different measuring conditions, i.e. e.g. in different magnetic field gradients in process step (A) and subsequently calculating the NMR spectra and fitting them to the NMR reference spectra by means of Gaus and Lorenz functions, thereby obtaining a mathematical function for the characteristic reference parameters of the reference spectra. When recording the NMR reference spectra for each individual lipoprotein class and lipoprotein subclass, the concentration of this lipoprotein class in the reference sample should be known. It is also possible to determine the reference parameters of individual lipoprotein classes from several reference samples in the case of unknown concentrations, using statistical methods.

As an alternative, it is also possible to calculate the characteristic parameters for each lipoprotein class by means of mathematical models rather than from reference samples (Gounarides et al., Nuclear magnetic resonance chromatography: applications of pulse field gradient diffusion NMR to mixture analysis and ligand-receptor interaction, Journal of chromatography B; 725 (1999), pages 79-90).

Advantageously, a mathematical function, the base function, which describes the characteristic reference parameters is obtained in the case of both alternative methods for the determination of the characteristic reference parameters. In process step B), the NMR spectra of the plasma or serum sample to be analysed can then be recorded under the same measuring conditions (identical magnetic field gradients and/or identical measuring temperature) as was the case with the reference samples or in the case of the calculation of the reference parameters by mathematical models, as the measuring conditions were set correspondingly in the mathematical models.

In process step C), calculated NMR spectra are fitted to the spectra determined in B) by way of a weighting of the reference parameters of each lipoprotein class. This weighting can be performed by modifying the base functions for each lipoprotein class and subclass, the base functions describing the characteristic reference parameters of each lipoprotein class, via proportionality factors for each base function in such a way that calculated NMR spectra can be fitted to the measured NMR spectra. These proportionality factors are then multiplied by weighting factors, calibration factors, from which direct conclusions can be drawn on the concentration of the lipoprotein classes concerned and their sizes and/or density distributions. In this way, the concentrations of particles of the individual lipoprotein classes and subclasses, their composition and density distribution and/or size distribution in a blood plasma or blood serum sample can be advantageously determined jointly.

In process steps A) and B), one-dimensional proton NMR spectra of reference samples and the serum or blood plasma samples to be analysed are advantageously detected for reasons of simplicity. In the case of one-dimensional NMR spectra, the decrease in transverse magnetisation, namely the free induction decay (FID), is detected during pulse Fourier transformation NMR, only one frequency variable being present in contrast to multidimensional NMR spectra (Hesse, Meier, Zeeh: Spektroskopische Methoden in der organischen Chemie (Spectroscopic methods in organic chemistry); $4^{th}$ edition 1991 Thieme-Verlag, page 132). Thus, 1-D NMR spectra are easier to record than multidimensional spectra. However, it is also possible to use multidimensional NMR spectra, e.g. HSQC pulse sequences (heteronuclear single quantum coherence spectroscopy) using not only $^{1}H$ nuclei, but also $^{12}C$ and $^{15}N$ nuclei in one variant of a process according to the invention. Multidimensional spectra are more time consuming to record but are capable of providing more detailed information on the particle properties.

It is possible by means of one variant of a process according to the invention to detect also the concentrations of non-lipoprotein components in the plasma sample or serum sample, in addition to the classification of the lipoproteins, the determination of the concentration and the composition of the lipoprotein particles of the individual classes and their size distribution and/or density distribution. For this purpose, NMR reference data sets for each non-lipoprotein component of known concentration are recorded, in a similar way to the lipoprotein classes, under the same measuring conditions as in process step B) and the characteristic reference parameters of each non-lipoprotein component concerned are then determined in a way similar to the lipoprotein components. These reference parameters are selected, similar to the lipoproteins, from the line widths, the chemical shifts of the NMR signals and the intensities of the NMR signals as a function of the magnetic field gradients. If, additionally, the NMR reference data sets of these non-lipoprotein components are available, the concentrations of these non-lipoprotein components can additionally be determined in process step C) together with a concentration of the lipoprotein components. The non-lipoprotein components can in this case be selected from metabolites, for example, lactate, alcohols, in particular ethanol, fatty acids, carbohydrates, pharmaceuticals and proteins. In addition, nucleic acids such as DNA and RNA can be determined either as single strands or double strands.

If additionally to the reference parameters of the lipoprotein components the reference parameters of the non-lipoprotein components are used in process step C) for fitting of the calculated NMR spectra to the NMR spectra to be analysed, then the accuracy of the fitting process can be increased. This has the consequence that more accurate results can be achieved regarding the concentrations and density distribution and/or size distribution of the lipoprotein components and non-lipoprotein components of the blood sample in process step C).

In the case of one variant of a process according to the invention, the magnetic field gradients exclusively are varied as measuring condition and the blood samples to be analysed are measured at a constant temperature. During this process, the different effects of the various magnetic field gradients on the intensity of the NMR signals of the individual lipoprotein classes are determined. In this case, it is advantageous to record four one-dimensional NMR spectra of an NMR sample to be analysed with no magnetic field gradients and with varying magnetic field gradients. However, less than four or more than four one-dimensional NMR spectra can also be recorded.

In addition, it is possible to use the differences in the longitudinal and transverse relaxation times by varying the measuring conditions in order to discriminate between the lipoproteins.

Another embodiment of the invention comprises an apparatus for the analysis of lipoprotein classes in body fluids including:
  a first device for determining NMR reference data sets for each lipoprotein class with the corresponding reference parameters as a function of different measuring conditions, the measuring conditions being selected from different magnetic field gradients and varying temperatures,
  a second device for recording the NMR spectra of a plasma sample or serum sample to be analysed under the different measuring conditions of the first device,
  a third device for classifying the lipoproteins, for determining the concentration of the lipoprotein particles of the individual classes, for determining the composition and density and/or size distribution for each lipoprotein class by means of fitting calculated NMR spectra to the NMR spectra determined in the second device by way of a weighting of the reference parameters determined with the first device.

In one embodiment of the apparatus of the invention,
  the first device is adapted to determine the above mentioned NMR reference data sets,
  the second device is adapted to record the said NMR spectra of the samples and
  the third device is adapted to carry out the respective processes of classifying the lipoproteins and determining their concentration, composition and their density and/or size distribution.

In a further embodiment of the apparatus of the invention,
  the second and/or third device is adapted to determine the effects of the different measuring conditions on the intensity and line forms of the NMR signals of the individual lipoprotein classes, and
  the third device is adapted to assign a density and/or size distribution to the individual lipoprotein classes on the basis of said different effects determined with the second and/or third device.

The first device is preferably an NMR spectrometer which is connected to a data processing facility. This facility calculates the corresponding base functions from the NMR spectra of the reference samples of the lipoprotein classes which describe the characteristic reference parameters of each lipoprotein class. Alternatively, the first device can comprise merely one data processing facility which determines the reference parameters e.g. from the above-mentioned mathematical models in such a way that no NMR reference spectra of reference samples need to be recorded.

The second device is preferably also an NMR spectrometer and the third device a data processing facility, e.g. a computer, which carries out the corresponding fitting of the calculated spectra to the spectra to be analysed and determined with the second device by way of a weighting of the base functions. Thereby it is possible to calculate the concentrations of the lipoprotein classes and their size and/or density distribution. In one embodiment of the apparatus, the first and second device or even all three devices can be implemented in one device.

Another subject matter of the invention comprises a process for the determination of the concentration of lipoprotein classes and lipoprotein subclasses in body fluids wherein characteristic reference parameters of an NMR spectrum are determined for each lipoprotein class and lipoprotein subclass and calculated NMR spectra are fitted to the measured NMR spectra of the plasma or serum sample to be analysed by weighting these reference parameters using weighting factors, the concentrations of the lipoprotein classes and lipoprotein subclasses are determined by means of the weighting factors.

The concentrations of the lipoprotein classes and lipoprotein subclasses can be determined in a simple way by means of a weighting of the base and class functions which describe these reference parameters, as it has already been described on pages 8 to 11. Thereby, it is possible to assign to the weighting factors the concentrations of the lipoprotein classes and lipoprotein subclasses in the blood. The reference parameters of the base functions are selected from: chemical shifts, NMR signal intensity and NMR signal width, those of the class function from the known dependence of the base functions building up on external parameters.

Advantageously, this further embodiment of the process according to the invention comprises the following process steps:

A1) Determining a NMR reference data set with the reference parameters characteristic of each lipoprotein class and/or subclass, B1) Determining at least one NMR spectrum of a plasma or serum sample to be analysed, C1) Fitting a calculated NMR spectrum to the NMR spectrum recorded in B1) by way of a weighting of the reference parameters obtained in A1).

In an advantageous embodiment of this process, it is possible to additionally modify measuring conditions selected from magnetic field gradients and measuring temperature, during the recording of the NMR spectrum of the blood plasma sample or blood serum sample to be analysed, in process step B1). In this case, additional information is obtained on the density distribution and/or size distribution of the lipoprotein classes and lipoprotein subclasses in the sample to be analysed, as it has already been described on pages 3-7. In doing so, in process step A1) the intensities of the NMR signals of each lipoprotein class and lipoprotein subclass are additionally determined in an analogous manner as a function of the magnetic field gradients and the line width of the NMR signals are determined as a function of the measuring temperatures. In process step C1), apart from the concentrations of the lipoprotein classes and lipoprotein subclasses, their density distribution and/or size distribution are determined by fitting the calculated NMR spectra to the NMR spectra determined in B1).

For this variant of the process according to the invention, all the embodiments and apparatuses can also be used, which were already mentioned above.

All the above-mentioned variants of the process and the apparatus according to the invention can also be used to determine the density distribution and/or size distribution as well as to determine the concentration of other inhomogeneous particles, apart from lipoproteins, in any desired complex, inhomogeneous mixtures.

In the following, the invention will be explained in further detail by way of embodiments and figures.

BRIEF DESCRIPTION OF THE DRAWINGS

FIG. 10 shows in table form the chemical shifts, the sizes and densities of lipoprotein classes and non-lipoprotein components which can be determined by a process according to the invention.

DETAILED DESCRIPTION OF THE PRESENTLY PREFERRED EMBODIMENTS

Figure 1:
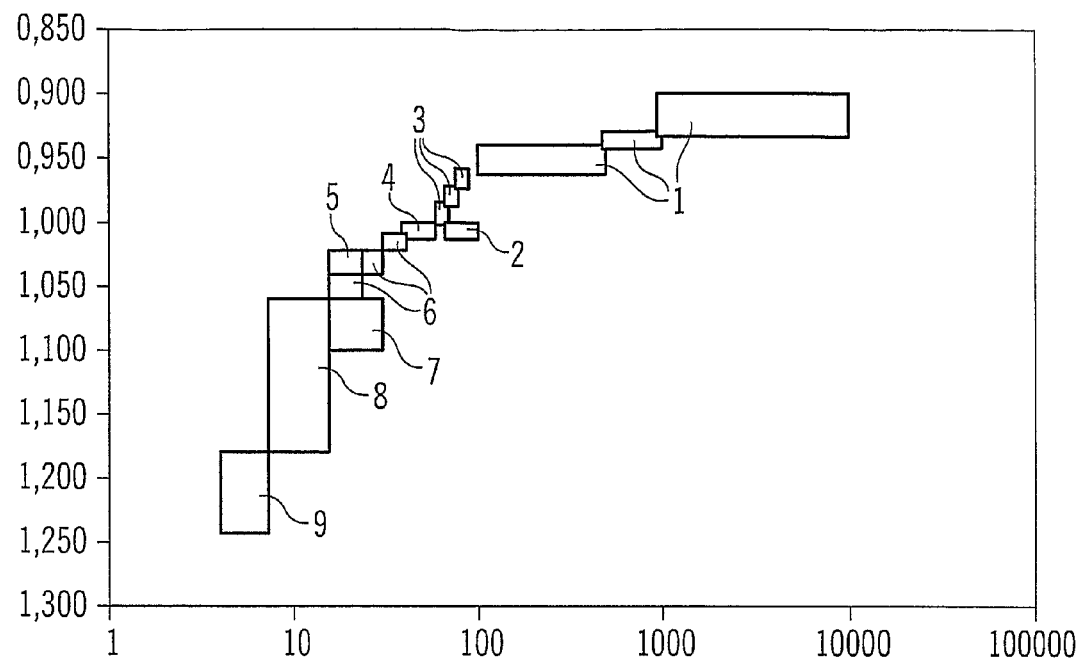
FIG. 1 shows a classification of the different lipoprotein classes into lipoprotein subclasses in the human blood which can be determined by a process according to the invention.

FIG. 1 shows a particle size distribution and density distribution of different lipoproteins detectable in the blood by process according to the invention. The particle diameter in μm is, in this case, plotted on the x axis and the particle density in g/cm$^3$ on the y axis. The density of the lipoprotein particles of different classes is essentially determined by their lipid composition. The areas indicated by 1 characterise the chylomicrons, the areas indicated by 2 the chylomicron remnants, the areas indicated by 3 the VLDL particles (very low density lipoproteins), the areas indicated by 4 the IDL particles (intermediate density lipoproteins), the bass indicated by 6 characterise the density distribution and particle size distribution of LDL particles, the area indicated by 5 the density distribution and particle size distribution of small dense LDL particles and the areas indicated by 8 and 9 the density distribution and particle size distribution of HDL2 and HDL3 particles. The area indicated by 7 characterises the Lp(a) particles.

The classification of the lipoproteins in the blood into lipoprotein classes has inter alia been described in the following publications: Kuller et al., (2002), Nuclear Magnetic Resonance spectroscopy of lipoproteins and risk of coronary heart disease in the cardiovascular health study, Ateriosler. Thromb. Vasc. Biol. 22, 1175-1180; Blake et al., (2002), Low-density lipoprotein particle concentration and size as determined by nuclear magnetic resonance spectroscopy as predictors of cardiovascular disease in women, Circulation 106, 1930-1937; Rosenson et al., (2002), Relations of lipoprotein subclass levels and low-density lipoprotein size to progression of coronary artery disease in the pravastatin limitation of arteriosclerosis in the coronary arteries (PLAC-I Trial), Am. J. Cardiol. 90, 89-94; Rosenson et al., (2002), Effects of pravastatin treatment on lipoprotein subclass profiles and particle size in the PLAC-I trial, Arteriosclerosis 160, 41-48. The classification of the different lipoproteins into lipoprotein classes on the basis of their density distribution and size distribution and apoprotein components varies, depending on the literature reference, the classification shown here having been carried out by the inventors. Depending on the requirements (e.g. more detailed classification of the HDL particles into more than two HDL subclasses HDL 2 und HDL3 for more detailed analyses), the classifications can be changed at will.

By way of one process according to the invention, all the particles shown in FIG. 1, in particular e.g. Lp(a) and small dense LDL which can be classified as being highly dangerous with respect to the risk for cardiovascular diseases, can be determined particularly reliably. The NMR signals of all these lipoprotein classes and lipoprotein subclasses exhibit an attenuation behaviour in magnetic field gradients which depends on the size distribution. In this respect, chylomicrons are so large that the intensities of their signals in NMR spectra of blood samples cannot influenced by applying magnetic field gradients, or hardly at all.

FIG. 2 shows schematically the course of a spin echo experiment with an applied magnetic field gradient. Such an experiment can be used in a variant of the process according to the invention for the selective suppression or attenuation of NMR signals of smaller lipoprotein classes. FIG. 2A shows how a $\pi/2$ pulse, a 90° pulse, is applied, the spins of the hydrogen atoms being rotated from the z direction into the detection plane, the x'-y' plane. A magnetic field $B_0$ is present on the sample in the z direction.

Figure 2C:
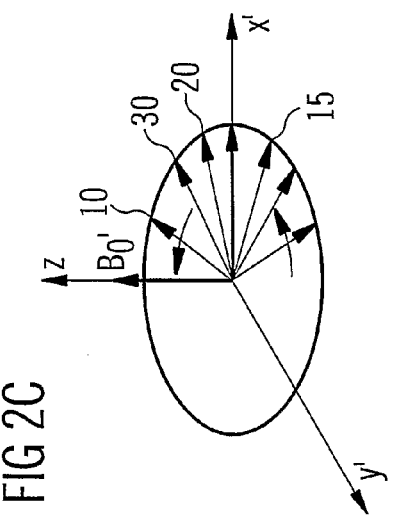
FIG. 2C shows schematically that, if during the divergence of the spin in the x'-y' plane, a magnetic field gradient $B_0'$ is applied along the z axis, additionally to the magnetic field $B_0$, the spins of different lipoprotein particles are situated in different magnetic fields, depending on their location.
Figure 2B:
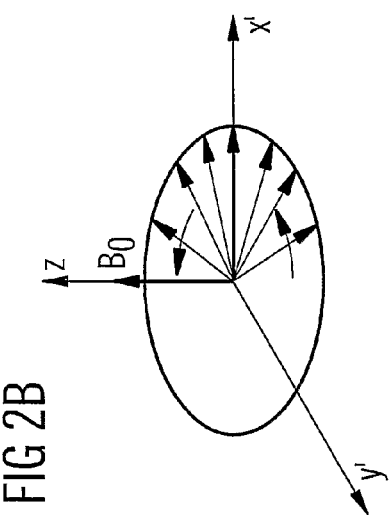
FIG. 2B shows how the spins immediately after the $\pi/2$ pulse process with a slightly different frequency in the x'-y' plane.
Figure 2A:
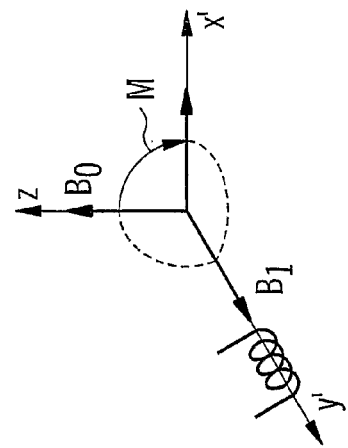
FIG. 2A shows how a $\pi/2$ pulse, a 90° pulse, is applied, the spins of the hydrogen atoms being rotated from the z direction into the detection plane, the x'-y' plane.

FIG. 2B shows how the spins immediately after the $\pi/2$ pulse precess with a slightly different frequency in the x'-y' plane. Meanwhile, a transverse relaxation, the decomposition of the FID (free induction decay) takes place in the x'-y' plane which is described by the transverse relaxation time T2. This FID in the time domain can be converted, by way of a Fourier transformation known to a person skilled in the art, into a conventional NMR spectrum in the frequency domain.

Figure 2E:
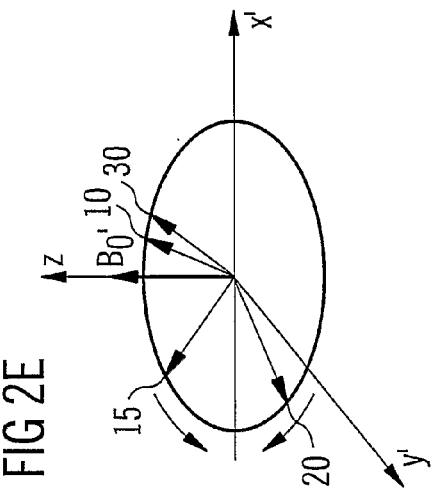
FIG. 2 shows schematically the course of a spin echo experiment with a magnetic field gradient.
FIG. 2D shows only spins 15, 20 of the larger lipoprotein particles are tilted over by 180° when a 180° pulse is applied such that only these are refocused resulting in a spin echo, as shown in FIG. 2E. In contrast, spins 10, 30 of the smaller lipoprotein particles which are already in another magnetic field, are not refocused.
Figure 2D:
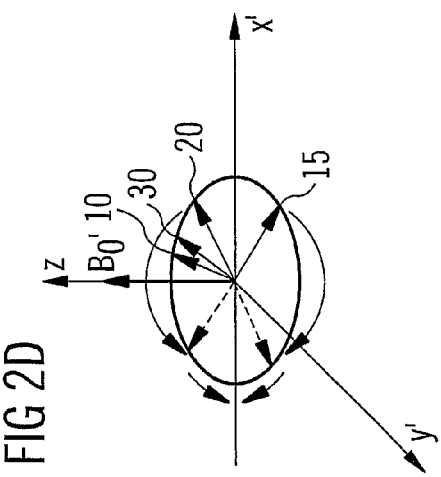

If, during the divergence of the spin in the x'-y' plane, a magnetic field gradient $B_0'$ is applied along the z axis, additionally to the magnetic field $B_0$, the spins of different lipoprotein particles are situated in different magnetic fields, depending on their location (FIG. 2C). The smaller and more compact lipoprotein particles (e.g. HDL particles) move, more rapidly, due to their increased diffusion, than corresponding larger lipoprotein particles (e.g. VLDL or LDL particles). FIG. 2C shows schematically that the spins 10, 30 of the smaller lipoprotein particles move more rapidly as a result of their increased diffusion than spins 15, 20 of correspondingly larger lipoprotein particles. Consequently, during the decay of the cross-magnetisation in the x'-y' plane, the different lipoprotein particles are situated at different sites as a result of the different diffusion-rates and are consequently under the influence of different z-magnetic field strengths. In particular, the precision phases of spins of smaller lipoprotein particles, which, due to their more rapid diffusion, are in an area with another magnetic field, cannot be fully refocused by a subsequent 180° pulse, a $\pi$-pulse, as shown in FIG. 2D. As a result, as shown diagrammatically in FIG. 2D, only spins 15, 20 of the larger lipoprotein particles are tilted over by 180° when a 180° pulse is applied such that only these are refocused resulting in a spin echo, as shown in FIG. 2E. In contrast, spins 10, 30 of the smaller lipoprotein particles which are already in another magnetic field, are not refocused. The consequence of this is that, depending on the intensity of the magnetic field gradients applied, the NMR signals of smaller lipoprotein particles which exhibit a higher rate of diffusion than larger lipoprotein particles can be selectively weakened or even completely suppressed.

Figure 3:
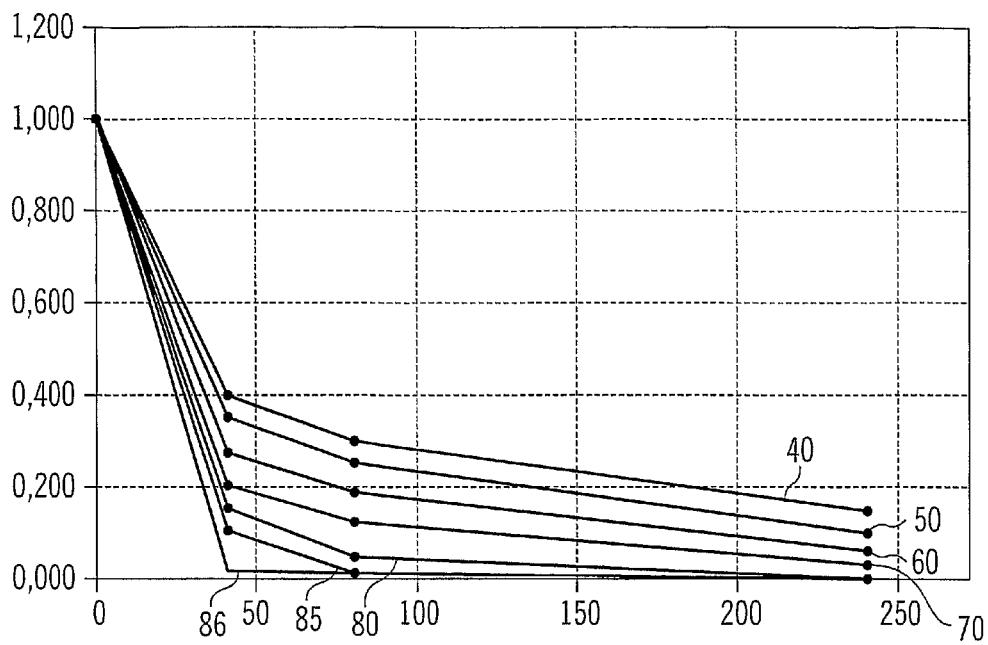
FIG. 3 shows the intensity behaviour of the NMR signals of different lipoprotein classes under the influence of no magnetic field gradients or magnetic field gradients of different strength.

FIG. 3 shows the decrease of NMR signals of different lipoprotein classes under the influence of gradient effects of different strengths. The relative signal intensity is plotted on the y-axis and the gradient effect (gradient strength x time) is plotted on the y axis. The curve indicated by 40 characterises the decrease in the signal intensity of chylomicron signals, the curve indicated by 50 the decrease in the signal intensity of NMR signals of VLDL-particles and the curve indicated by 60 the decrease in the NMR signal intensity of IDL particles. The curve indicated by 70 is the signal intensity of LDL particles and the curves indicated by 80 and 85 the decrease in the signal intensity of HDL2 and HDL3 particles as a function of the strength of the magnetic field gradients.

For purposes of clarity, the decrease in the signal intensities of some other substances contained in the serum, which do not belong to the lipoprotein fraction, has been characterised by 86. These substances would be found in experiments in a lipoprotein-free serum (LPDS=lipoprotein deficient serum). It can be clearly seen from the curves that the attenuation of the NMR signals increases with a decreasing size of the lipoprotein particles and an increasing magnetic field gradient.

Figure 4:
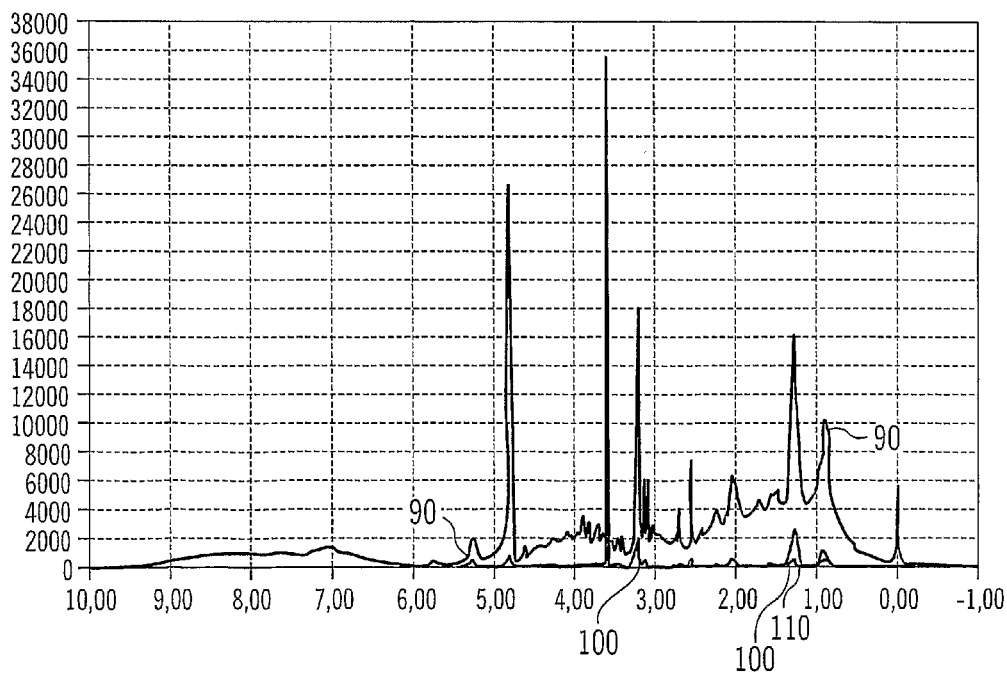
FIG. 4 shows different one-dimensional NMR $^1$H spectra of a blood plasma sample with and without magnetic field gradients.

FIG. 4 shows different one-dimensional $^1$H NMR spectra of a blood plasma sample recorded without and with magnetic field gradients. In FIG. 4 and all subsequent figures which show NMR spectra, the chemical shift is plotted in ppm on the x axis and the intensity on the y axis. The one-dimensional NMR spectrum indicated by 90 was recorded without magnetic field gradients and the NMR spectra indicated by 100 and 110 with magnetic field gradients rising from 100 to 110. It can be seen that with rising magnetic field gradients, the signals of all small substances dissolved in the blood (proteins, salts, amino acids) which are smaller than 1 nm, can be suppressed almost completely.

Figure 5:
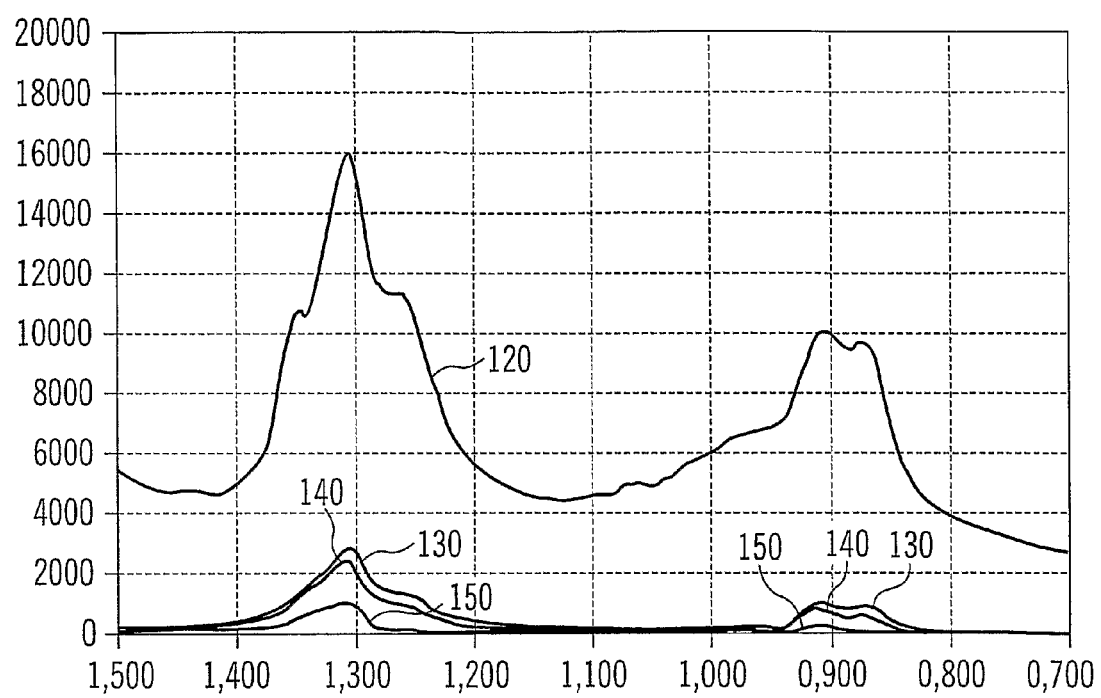
FIGS. 5 and 6 show the region of the methyl and methylene signals of NMR-$^1$H spectra of a blood plasma sample recorded with and without magnetic field gradients.
Figure 6:
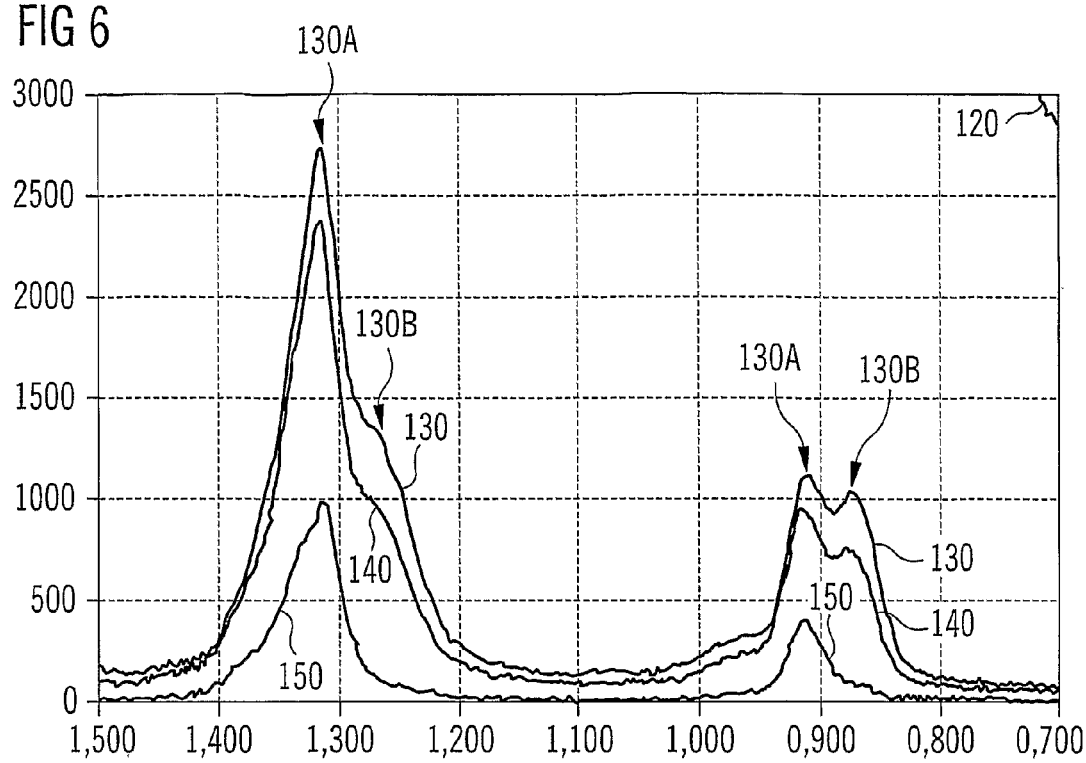

FIGS. 5 and 6 show the same region of 1.4 ppm to 0.8 ppm in a $^1$H-NMR spectrum, the area of the methyl and methylene peaks of the lipoprotein classes present in the blood. In FIG. 6, the area shown in FIG. 5 is illustrated enlarged. The spectrum indicated by 120 was recorded without magnetic field gradients and the spectra indicated by 130, 140 and 150 with rising magnetic field gradients. It can be clearly seen that the signal intensity of all signals decreases with an increasing magnetic field gradient. In FIG. 6, the NMR signals characterised by 130A represent the methyl and methylene peaks of VLDL particles and the signals characterised by 130B the methyl- and methylene peaks of HDL particles. In this case, the HDL particles are much smaller than the VLDL particles (see e.g. FIG. 1). FIG. 6 clearly shows that the intensity of the HDL signals decreases more strongly with a rising magnetic field gradient than the intensity of the corresponding VLDL signals. In the case of the spectrum indicated by 150, which was recorded at the strongest magnetic field gradient, the HDL signals are almost fully suppressed.

Figure 7:
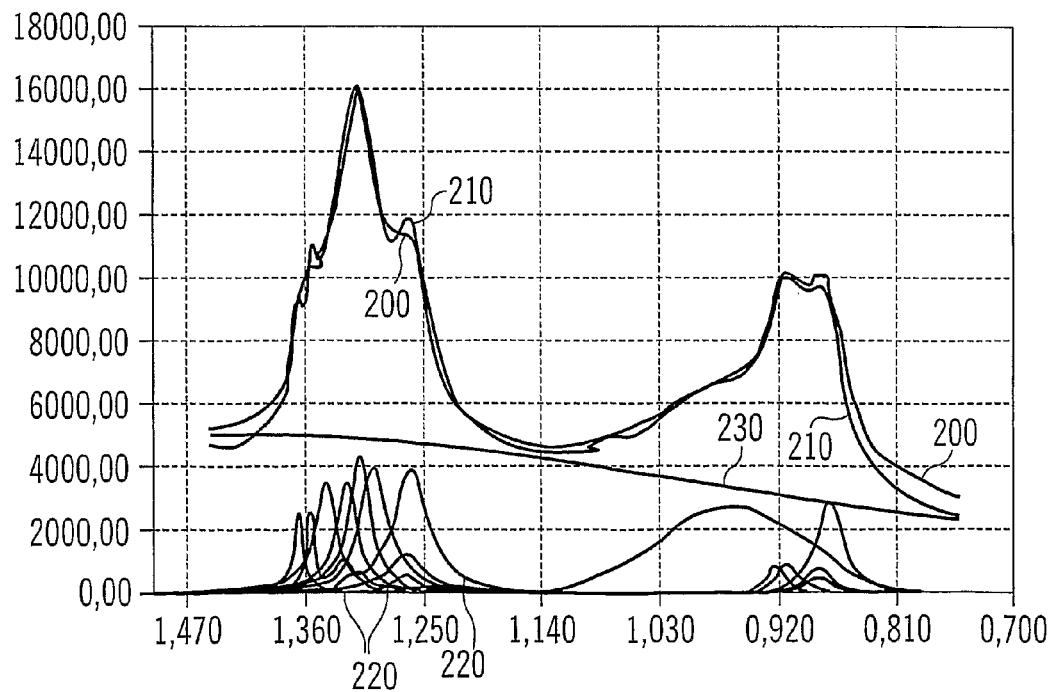
FIGS. 7 and 8 show the fitting of a calculated spectrum to an NMR spectrum to be analysed by means of a weighting of the class functions of the individual lipoprotein classes.

FIG. 7 shows the approximation of a calculated spectrum 210 to a spectrum of a blood plasma sample or serum sample 200 to be analysed. In this case, the approximation is carried out by means of a variation and addition of different base functions 220 for the individual lipoprotein classes. The line indicated by 230 shows the background of the measurement, which is still fairly strong in FIG. 7 since the NMR spectrum was recorded without magnetic field gradient.

Figures 8, 9:
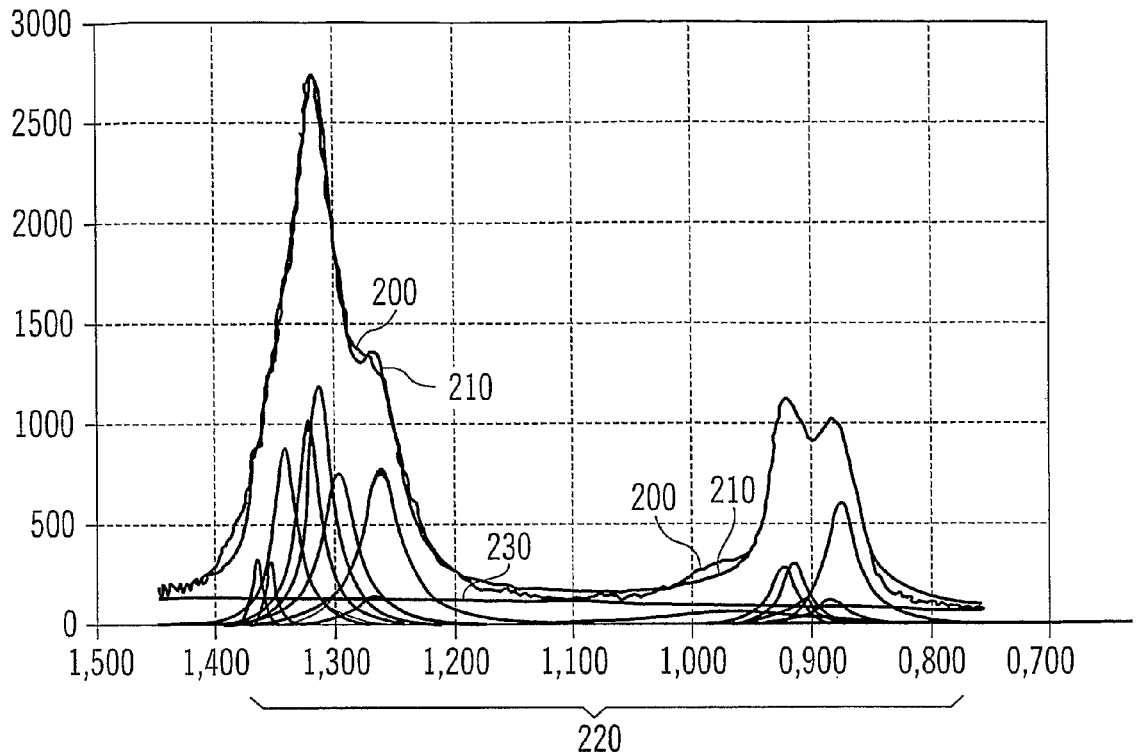
FIG. 9 shows, as an example, an NMR reference data set with characteristic reference parameters for a lipoprotein subclass.

FIG. 8 shows the NMR spectrum already shown in FIG. 7 though under the influence of slight magnetic field gradients. The intensity of the background 230 has decreased correspondingly since the signal intensity of the NMR signals of the small dissolved substances is being almost completely suppressed.

FIG. 9 shows as an example the NMR reference data set of a lipoprotein subclass LDL[A], which contains the characteristic reference parameters of this lipoprotein subclass. The line characterised by "standard without gradient" indicates the signal intensity of the methyl and methylene signals without magnetic field gradient, whereas "standard gradient [A]" to "standard gradient [C]" shows the corresponding reference parameters for the signal intensity of the NMR signals with three magnetic field gradients rising from [A] to [C]. A further characteristic reference parameter is the line width and the chemical shift, in ppm. Moreover, the proportion of the Lorenz and Gaus functions in the base function is indicated. Such an NMR reference data set can be drawn up for each lipoprotein class and/or subclass. Analogous reference data sets can also be drawn up for non-lipoprotein components of the blood plasma sample or serum sample, e.g. lactate and other proteins.

FIG. 10 shows a list of 15 lipoprotein classes and/or lipoprotein subclasses and their respective minimum and maximum sizes in nm, minimum and maximum densities in g/ml and the corresponding chemical shifts of their methyl and/or methylene NMR signals. The classification of the lipoproteins into lipoprotein classes, e.g. HDL and further into the corresponding lipoprotein subclasses, e.g. HDL2 and HDL3, on the basis of density distributions and size distributions has been carried out by the inventors. Such class and subclass classifications can be subdivided and/or simplified even further, depending on the requirements. By means of one process according to the invention, the exact size distribution and density distributions for each lipoprotein class and subclass can be determined which can also be an indicator of the susceptibility to certain cardiovascular diseases. Moreover, other constituents can also be determined, e.g. the smaller LPDS with a diameter of <1 nm, which are dissolved in the blood. Additionally, lactate and unsaturated fatty acids [A] and unsaturated fatty acids [B] are listed.

Embodiment

Under standardised conditions (e.g. after 12 hour fasting, before or after the application of active substances), >1 ml of blood is taken from the candidate and kept cool on ice. Using standard methods, blood plasma or blood serum is obtained, the blood serum is stored under cool conditions (at 277 K). Before the measurement, 50 µl of a standard mixture A (0.01 M DSS in $D_2O$) are added to 400-450 µl of blood plasma or blood serum in Eppendorf pipettes and mixed. This mixture is then transferred into a 5 mm NMR tube and placed into the NMR spectrometer. Alternatively, continuous flow systems can also be used in the case of which a pipetting robot supplies the standard mixture through a pipette and transfers it in a defined quantity into the NMR spectrometer. During this process, the measuring temperature is simultaneously set. The samples are then measured at 308 K. A 1D $^1$H NMR spectrum is recorded on the NMR spectrometer (resolution: 32768 data points with 0.37 Hz/point, a spectral width of 12000 Hz, 10 µs 90° pulse, d1 delay of 0.7 s and a recording time of 1.36 s). Using the same spectral parameters, 3 diffusion-weighted 1D $^1$H NMR measurements are additionally carried out with a modified STE-LED (stimulated Echo and Longitudinal Eddy-current delay) pulse sequence. The diffusion-weighted gradients in this case amount to 40% (40 G/cm) with a length of 2 ms (experiment 2), 80% (80 G/cm) with a length of 2 ms (experiment 3) and 80% (80 G/cm) with a length of 3 ms (experiment 4). The FIDs (free induction decay) measured are filtered digitally, Fourier transformed and processed with the spectrometer-specific software (phase correction and baseline correction). These spectra are then converted into an ASCII format, then loaded into a PC. Here they are evaluated with the concentration-weighted multidimensional class functions. The particle concentrations of the different lipoprotein classes which are obtained are then printed out together with other parameters (e.g. lipid composition).

The scope of protection of the invention is not limited to the examples given hereinabove. The invention is embodied in each novel characteristic and each combination of characteristics, which particularly includes every combination of any features which are stated in the claims, even if this feature or this combination of features is not explicitly stated in the claims or in the examples.

The invention claimed is:

1. A process for the determination of lipoprotein classes in a body fluids sample, comprising
    measuring the NMR spectra of the body fluid sample under different measuring conditions which are selected from the group consisting of different magnetic field gradients and varying temperatures and
    determining characteristic reference parameters for each individual lipoprotein class based on the different effects of these measuring conditions on the intensity and line forms of the NMR spectra of the individual lipoprotein class and assigning a density distribution and/or size distribution to the individual lipoprotein classes on the basis of the characteristic reference parameters.

2. The process according to claim 1, wherein
    characteristic reference parameters of an NMR spectrum are determined beforehand for each lipoprotein class to be analysed; and the measured NMR spectra of the body fluid sample to be analysed are fitted using calculated NMR spectra which are obtained by varying and combining these characteristic reference parameters.

3. The process according to claim 2, wherein
    the characteristic reference parameters are selected from the group consisting of:
    chemical shift, NMR signal intensity and NMR signal form as a function of magnetic field gradients.

4. The process according to claim 1 including the process steps of:
    A) Determining an NMR reference data set for each lipoprotein class with the characteristic reference parameters and calculating the effects of the different measuring conditions on the signal intensity and/or line widths of each lipoprotein class as a function of its size distribution and/or density distribution on the basis of the reference parameters,
    B) Calculating an NMR reference spectra based on the NMR reference data set;
    C) Determining the NMR spectra of the body fluid sample under the different measuring conditions used in A),
    D) Fitting the calculated NMR spectra to the spectra determined in C) by means of a weighting of the reference parameters of each lipoprotein class.

5. The process according to claim 4, wherein
in process step A), the NMR reference data set for each lipoprotein class are recorded under the different measuring conditions and the calculated NMR spectra are fitted to the NMR reference spectra by way of a sum of frequency-shifted and intensity-weighted base functions, a mathematical function being obtained for the characteristic reference parameters of the reference spectra.

6. The process according to claim 4, wherein
in process step A), the characteristic reference parameters of each lipoprotein class are calculated using mathematical models.

7. The process according to claim 4, wherein
in process step D), calculated NMR spectra are fitted to NMR spectra of the body fluid sample, detected in C), by weighting the characteristic reference parameters on the basis of weighting factors, and
the density and/or size distribution of the individual lipoprotein classes in the body fluid sample is determined using the weighting factors determined.

8. The process according to claim 7, wherein
in process step D) the concentrations of the individual lipoprotein classes are additionally obtained.

9. The process according to claim 4, wherein
in process steps A) and C) 1D NMR spectra of reference samples and body fluid samples to be analysed are detected.

10. The process according to claim 4, wherein
the concentrations of non-lipoprotein components in the body fluid sample are additionally determined.

11. The process according to claim 10 wherein
NMR reference data sets for each non-lipoprotein component with the characteristic reference parameters is determined in process step A), and
in process step D), the concentrations of the non-lipoprotein components are additionally determined.

12. The process according to claim 10, wherein
the non-lipoprotein components are selected from the group consisting of organic molecules, alcohol, amino acids, peptides, nucleic acids, fatty acids, carbohydrates, pharmaceuticals and proteins.

13. The process according to claim 1, wherein
the lipoprotein classes are selected from the group consisting of:
chylomicron-A, chylomicron-B, chylomicron-C, chylomicron remnants, VLDL-A, VLDL-B, VLDL-C, IDL, small dense LDL, LDL-A, LDL-B, LDL-C, HDL-2, HDL-3 and Lp(a).

14. The process according to claim 1, wherein
the magnetic field gradients are varied exclusively as measuring conditions and the different effects of the various magnetic field gradients on the intensity of the NMR signals of the individual lipoprotein classes are determined.

15. The process according to claim 14, wherein
at least four 1D NMR spectra of the body fluid sample are recorded with different magnetic field gradients in each case.

16. The process according to claim 1, wherein
the density distribution and/or size distribution and the concentration of other in-homogeneous particles other than lipoproteins in the body fluid sample are determined by measuring the NMR spectra of the body fluid sample under the different measuring conditions as used to determine the density and/or size distributions of the lipoprotein classes.

17. The process according to claim 1, wherein
variations in the T1 and T2 relaxation times observed in the NMR spectra of the body fluid sample under the different measuring conditions are used for assigning a density distribution and/or size distribution to the individual lipoprotein classes.

18. An apparatus for the analysis of lipoprotein classes in a body fluid sample comprising:
a first device for detecting NMR reference data sets and characteristic reference parameters for each lipoprotein class as a function of different measuring conditions which are selected from the group consisting of different magnetic field gradients and varying temperatures,
a second device for detecting the NMR spectra of the body fluid sample under the same different measuring conditions as used in the first device, and
a third device for calculating an NMR spectra based on the NMR reference data, comparing the calculated NMR spectra to the NMR spectra of the body fluid sample detected in the second device by weighting with the characteristic reference parameters determined with the first device, and determining the concentrations and density and/or size distributions for each lipoprotein class in the body fluid sample based on the comparison.

19. The apparatus according to claim 18, wherein
the first device comprises means for calculating the effects of the different measuring conditions on each lipoprotein class as a function of its density and/or size distribution,
the second device comprises means for detecting the actual effects of the different measuring conditions on each lipoprotein class in the body fluid sample as a function of its density and/or size distribution, and on each lipoprotein class,
the third device
contains means for fitting the calculated effects determined by the first device to the effects actually determined by the second device, by way of a weighting of the characteristic reference parameters by weighting factors and
means for calculating the density and/or size distribution of each lipoprotein class in the body fluid sample using the weighting factors.

20. The apparatus according to claim 18, wherein
the first and/or second device comprises an NMR spectrometer,
the third device comprises a data processing facility.

21. A process for the determination of the concentrations of lipoprotein classes and subclasses in a body fluid sample comprising:
determining characteristic reference parameters of an NMR spectrum for each lipoprotein class and subclass to be analyzed, the characteristic reference parameters being determined using different and independent measuring conditions from those used in an apparatus to record measured NMR spectra of a body fluid sample, measuring the NMR spectra of the body fluid sample, calculating NMR reference spectra for each lipoprotein class and subclass using the characteristic reference parameters, and fitting the measured NMR spectra of a body fluid sample to the calculated NMR reference spectra by means of a weighting of the characteristic reference parameters using weighting factors in order to determine the concentrations of the lipoprotein classes and subclasses in the body fluid sample.

22. The process according to claim 21, wherein the characteristic reference parameters are selected from: chemical shift, NMR signal intensity and NMR signal form.

* * * * *